United States Patent [19]

Latura et al.

[11] Patent Number: 5,268,300

[45] Date of Patent: Dec. 7, 1993

[54] AUDITING CONTAMINATED WATER EFFLUENTS FOR FEASIBLE REUSE

[75] Inventors: William D. Latura, Bloomingdale; Theodore A. Voruz, Naperville; Abram R. Glazer, Chicago, all of Ill.

[73] Assignee: Nalco Chemical Company, Naperville, Ill.

[21] Appl. No.: 987,581

[22] Filed: Dec. 8, 1992

Related U.S. Application Data

[63] Continuation of Ser. No. 726,846, Jul. 8, 1991, abandoned.

[51] Int. Cl.⁵ .................... G01N 35/08; G01N 33/18; C02F 9/00; C02F 1/00
[52] U.S. Cl. ..................................... 436/53; 73/61.62; 210/96.1; 210/241; 210/739; 422/24; 422/62; 422/81; 422/82; 436/38; 436/39; 436/55; 436/172; 436/175
[58] Field of Search ............... 73/61.62; 210/96.1, 210/195.1, 241, 257.1, 258, 805, 806, 739; 422/68.1, 24, 62, 81, 82; 436/38, 39, 53, 55, 172, 175

[56] References Cited

U.S. PATENT DOCUMENTS

| | | | |
|---|---|---|---|
| Re. 33,346 | 9/1990 | Knudsen et al. | 422/53 X |
| Re. 33,468 | 12/1990 | Brindak | 73/61.2 |
| 3,630,365 | 12/1971 | Woodbridge | 210/241 |
| 4,383,920 | 5/1983 | Muller et al. | 210/96.1 X |
| 4,400,270 | 8/1983 | Hillman | 436/55 X |
| 4,659,460 | 8/1987 | Muller et al. | 210/241 X |
| 4,722,830 | 2/1988 | Urie et al. | 422/62 |
| 4,764,271 | 8/1988 | Acosta | 210/96.1 X |
| 4,780,200 | 10/1988 | Bond et al. | 422/24 X |
| 4,783,314 | 11/1988 | Hoots et al. | 422/62 X |
| 4,849,114 | 7/1989 | Zeff et al. | 422/24 X |
| 4,931,187 | 6/1990 | Derham et al. | 210/96.1 X |
| 4,999,103 | 3/1991 | Bogart | 210/241 X |
| 5,041,386 | 8/1991 | Pierce et al. | 436/50 |
| 5,057,229 | 10/1991 | Schulenburg | 210/96.1 X |
| 5,141,653 | 8/1992 | Smith et al. | 210/806 |
| 5,145,585 | 9/1992 | Coke | 210/803 X |

Primary Examiner—James C. Housel
Assistant Examiner—Arlen Soderquist
Attorney, Agent, or Firm—Kinzer, Plyer, Dorn, McEachran & Jambor

[57] ABSTRACT

Apparatus and method for practice in an over-the-road vehicle to determine whether effluent water released in an operating water treatment system (plant installation) can be adequately treated to remove contaminants so the effluent may be reused at the plant rather than discharged to the environment with inimical effect. The frame of the vehicle supporting a plurality of clean holding tanks, a plurality of functionally different water treating units, an analysis laboratory, a pilot cooling tower simulator, and a pilot boiler simulator. The effluent is transferred from one of the holding tanks to at least one of the water treating units to reduce the contaminant level. When the contaminant level has been reduced to a level appropriate for reuse at the plant, the effluent is transferred to one of the simulator apparatus for evaluation of the treated water in the corresponding plant process.

10 Claims, 3 Drawing Sheets

AUDITING CONTAMINATED WATER EFFLUENTS FOR FEASIBLE REUSE

This is a continuation of copending application(s) Ser. No. 07/226,846 filed on Jul. 8, 1991, now abandoned.

This invention relates to vehicle mounted apparatus for auditing the water effluent stream from a water treatment system. Typical effluent streams to be analyzed would be derived from process waters contaminated by undesirable components. The effluent may be one presently intended for discharge to the environment, but which, due to increasingly stringent environmental standards, must be prepared for other means of disposal.

Under the present invention, the effluent is audited on-site to determine if it is susceptible to treatment to reduce the contaminants to such levels that the effluent may be returned to the system for reuse.

While mobile systems for an on-site audit of heat exchange efficiency have previously been proposed (Patent Nos. Re. 33,346 and Re. 33,468), there has to the best of our knowledge been no audit apparatus subscribing to the following conditions and arrangement.

SUMMARY OF THE DISCLOSURE

The apparatus of the present invention includes holding or equalizing tanks for the effluent sampled on-site and for samples treated under the present invention, means to transfer a sample to functionally different water treatment units for separation of contaminants in the form of solids, destruction of unwanted organics and nutrient support for low plant or animal life which thrive on unwanted organics.

The apparatus includes a laboratory where grab samples of the effluent are initially tested to determine a treatment protocol, to analyze the results of any treatment (unit or combined treatments) and to determine if there is indeed a feasible treatment program.

The apparatus includes a process simulator (pilot plant installation) which simulates a plant water cooling tower or boiler.

A water cooling tower is shown in U.S. Pat. No. 4,783,314, the disclosure of which is incorporated herein by reference. A boiler is shown in application Ser. No. 286,034, filed Dec. 19, 1988 now U.S. Pat. No. 5,041,386, and the disclosure is also incorporated herein by reference.

INTRODUCTION

Figure 1:
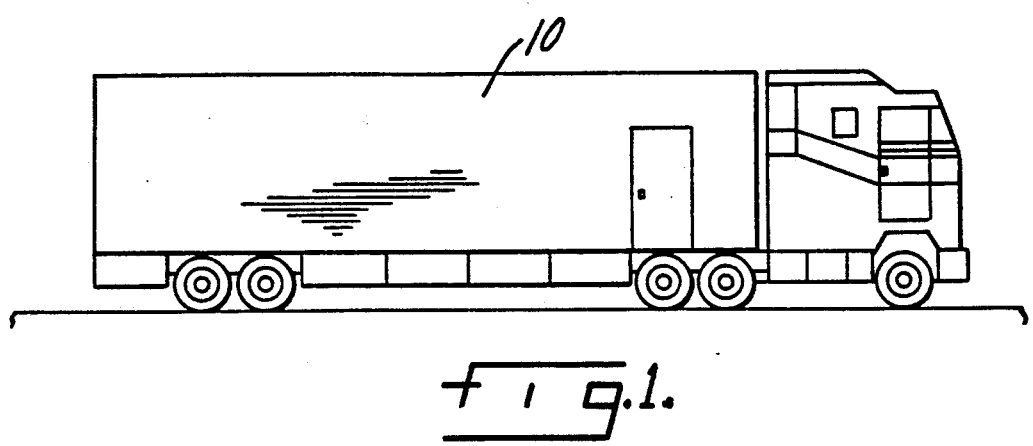
FIG. 1 is an elevation of a semitrailer in which the present apparatus may be embodied.

A vehicle which can be employed in the practice of the present invention is shown in FIG. 1 as a large van or semitrailer 10. Holding or flow equalizing tanks (as will be described) are removably supported beneath the frame of the trailer. Water treatment units, functionally of different kinds, are housed within the trailer above the tanks along with analyzers (as will be described) for determining the quality of the water so treated. Process simulation apparatus, either a pilot water cooling tower or pilot boiler, is also staged in the trailer so that a corresponding plant process may be run on a real time basis, using the treated water.

The vehicle will be moved from one plant site to another where effluent water samples at the plant sites are withdrawn, passed to a selected one of the holding tanks and pumped from the tank to a selected one of treatment units were the effluent water is treated to remove the contaminants. The treated water is analyzed to determine if it is feasible to treat the effluent water, or if stronger treatment is required, so that the effluent may be recirculated or otherwise used at the plant site rather than being discharged to the environment.

Figure 2:
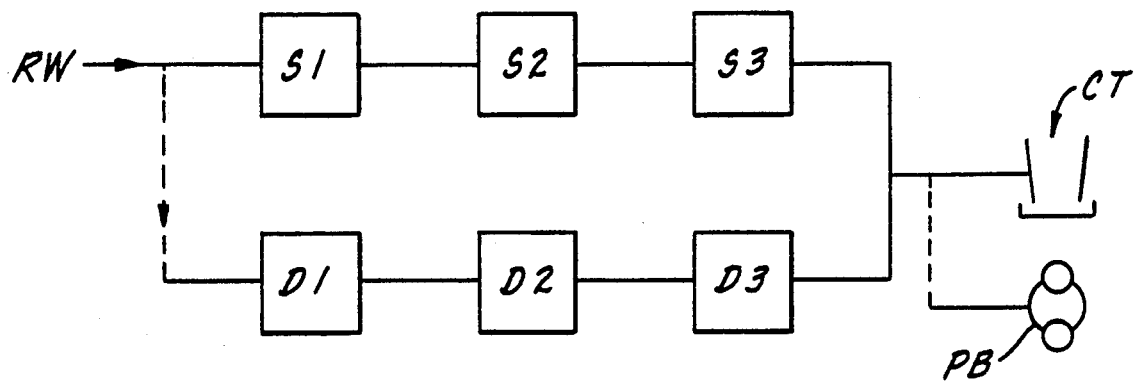
FIG. 2 is a diagram illustrating principles of the invention.

The general arrangement is introduced by what is shown schematically in FIG. 2. The effluent or raw water to be analyzed, RW, is subjected to either a separation process (treating units S1, S2, S3 and so on; a filters or clarifiers) and/or the effluent is subjected to a destructive process to eliminate unwanted organics such as amines, hydrocarbons, phenols and so on (D1, D2, D3 and so on; treatment by oxidation, ozonation, pH control), peroxides, ultraviolet light).

The apparatus, FIG. 2, may be employed in different ways, successive treatments S1 and S2, or D1 and D3; or the treatments may be of cross succession, viz. S1, D2, S3.

In any event after one treatment is completed, say S1, the sample so treated will be returned to a tank and its contents as a second sample them pumped to a second treating unit. Thus, in the simple case of two separation treatments one is undertaken, say S1, FIG. 2, the contents after treatment are returned to a tank, and its contents then pumped from that tank to the second separation treatment unit, S2. Likewise, if the program is destructive of organics, D1 and D2.

DETAILS

Figure 3:
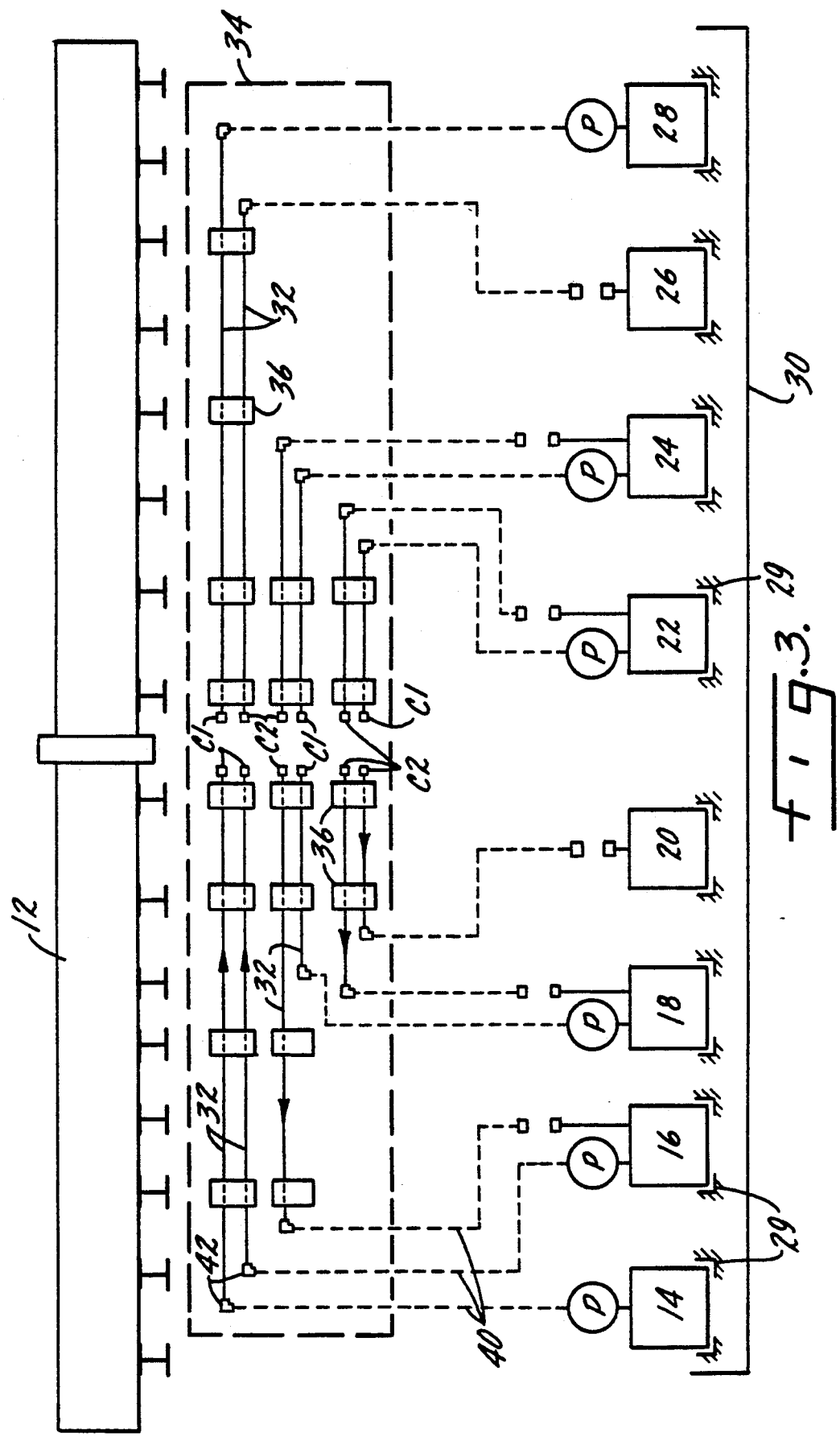
FIG. 3 is a plan view of the equalizing or holding tanks and the arrangement of manifolds by which the contents of the holding tanks may be pumped to or received from one of the treating units, one or both simulation pilots and the water used in the laboratory.

In FIG. 3 the trailer bed is indicated at 12. The equalizing tanks referred to above for receiving the contaminated effluent sample to be transmitted to a treating unit, and for receiving water treated within the vehicle, are identified by reference characters 14, 16, 18, 20, 22, 24, 26 and 28.

As will be explained below, the apparatus may include simulation apparatus for evaluating characteristics of the water treated by a treating unit, and such evaluating apparatus may include a pilot cooling tower or a pilot boiler CT and PB respectively, FIG. 2. Equalizing tanks 22 and 24 are assigned to the evaluating equipment.

Tanks 26 and 28 are laboratory dedicated for receiving waste water and supplying potable water, respectively.

All tanks are removably supported on guides 29 and of course are locked in place above a water sealed sump 30. After a particular plant site is audited, the tanks are emptied and rigorously cleaned.

An arrangement of lower manifolds or conduits 32 are strung beneath the trailer frame (collectively identified by reference character 34) and are secured in place by clamps 36 to the underside of the vehicle frame. The outlets of the pumps are manually connected by braided hoses as 40 to elbows 42 at the receiving end of the related manifold and each such manifold terminates at the underside of the trailer frame in a connector C1 for transmitting a sample from a tank to a paired connector C11, FIG. 4.

Figure 4:
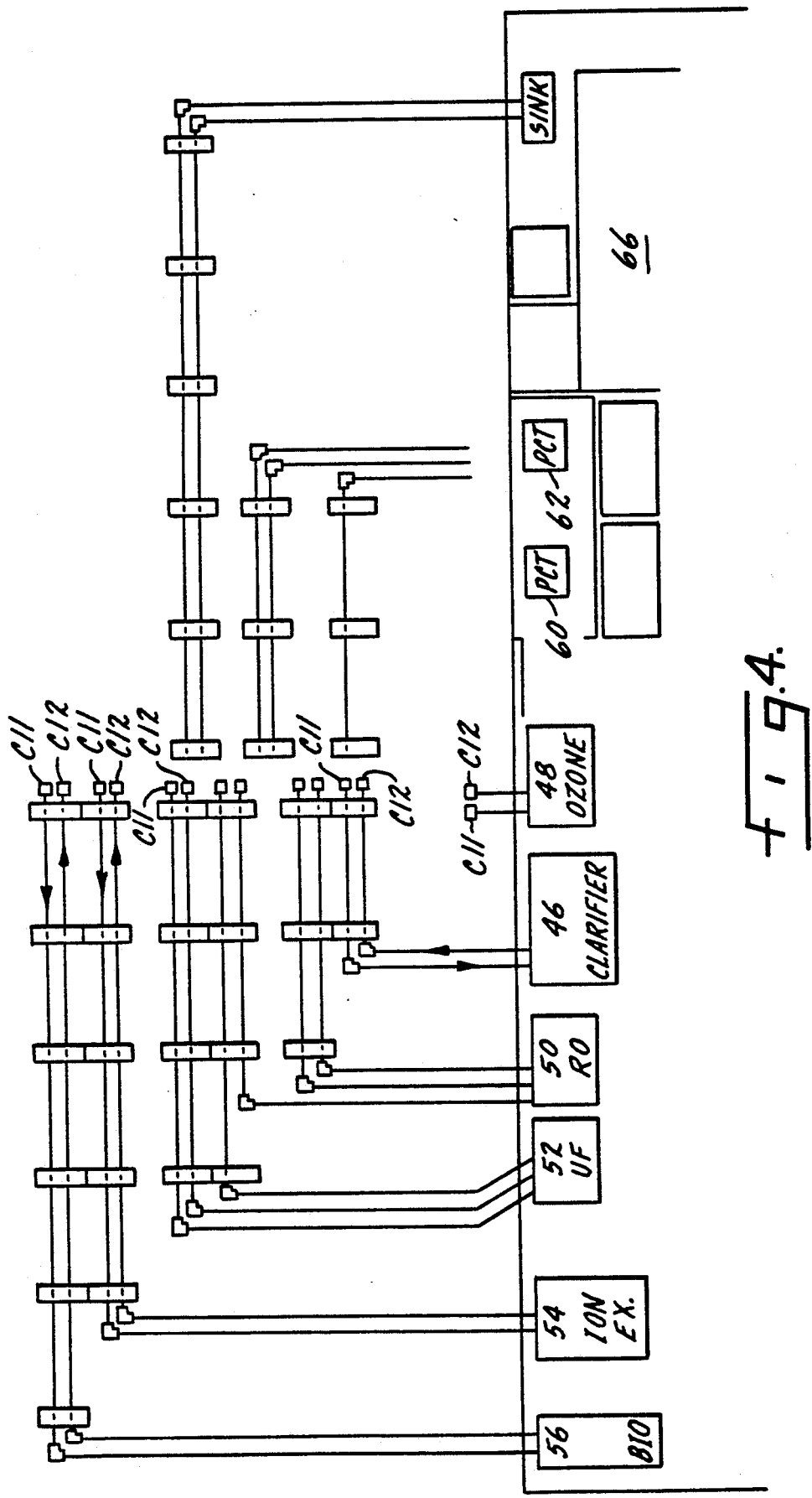
FIG. 4 is a plan view of the treating units, the pilot installations, the laboratory within the vehicle and the manifolds and connectors identified with the tanks shown in FIG. 3.

For example, the flexible braided hose which is identified with the clarifier 46 will be joined to its connector C11, FIG. 4, so that the sample effluent in tank 16, FIG. 3, may be pumped to the clarifier 46.

Thus, each of the tanks 16 and 18 for example has a manifold outlet connector C1, FIG. 3, for passing an effluent sample to a treating unit connector C11, FIG. 4, which leads the sample to a treating unit, and in like manner there will be a connector C12, FIG. 4, for returning the treated water to a tank. It is the intention of this disclosure to indicate this uniformity of selection possibilities (C1 to C11) between the various holding tanks and the treating units 46, 48, 50, 52, 54 and 56 shown in FIG. 4. Likewise as return (C12 to C2) from a treating unit back to a tank. A specific example will be given below in which the effluent treated at the clarifier 46, received from tank 14, may be returned to another tank as 16 and the contents then pumped therefrom to the ultrafine filter 52. The clarifier separates large particles (usually larger than 0.5 microns) while unit 52 separates particles which takes out solids of colloidal size in the range of 0.05 to 0.1 microns.

Thus, the clarifier 46 and the ultrafine filter 52 represent separation treatments. The treatment is a coagulant. Separation is equally true of treating unit 50 (RO, "reverse osmosis" which may be employed to remove dissolved contaminants or for sea water desalinization). Treating unit 50 thus injects, selectively, scale inhibitors, pH controllers and biocides. The ion exchange treating unit 54 is employed for removal of soluble ionic species. Strong acid, weak acid, strong base and weak base resins are employed. It embodies an absorption column configuration.

In comparison, the ozone treating unit 48 is another destruction unit in which inimical organics are destroyed, selectively, by ozonation or by ultraviolet light, or by peroxide or by pH control or any combination.

Treating unit 56 is employed to feed nutrients to low plant life which also destroy unwanted organics such as hydrocarbons.

Again, a particular treatment and analysis procedure may be as follows.

EXAMPLE 1

Separation (1) the raw effluent will be transferred from the plant site to tank 14, partially filling the tank.

(2) The pump P identified with tank 14 will transfer the effluent to the clarifier 46 by way of the related braided hosing 40, elbow 42, manifold 32 and finally through the braided hosing which joins connectors C1 and C11 leading to the input of the clarifier 46.

(3) Following the clarification treatment (for example treatment by a flocculent) a sample of the result will be taken and analyzed for effectiveness of the treatment in the laboratory in the vehicle, as hereinafter described.

Regardless of the efficacy of the clarification treatment, the contents so treated are returned to tank 16 by way of connection C12 (from the clarifier) to connection C2 which leads back to tank 16.

In all instances (tanks 14, 16, 18) connectors C1 and C11 transfer from a tank to a treating unit; connectors C2 and C12 are in the return lines back to a tank.

EXAMPLE 2

Destruction

1. Use either tank 14 or 16, say tank 14;
2. Transfer to 48 (ozone treatment) then back to tank 16;
3. If further treatment at 56 ("nutrient feed") is needed, pump from tank 16 to tank unit 56 and return to tank 16.

EXAMPLE 3

Examples 1 and 2 are combined so that both separation and destruction are applied to the sample.

PROCESS SIMULATION

The laboratory with the vehicle will report the proposed sequence (configuration) of unit treatments configured to the laboratory analysis of the effluent water. This report or recommendation will be based on an initial analysis of the plant effluent.

The configured results are stored in one of the tanks 22, 24 and the water so treated is then employed as the source water for a pilot cooling tower (or pilot boiler) within the vehicle. There are two pilot cooling towers 60 and 62, FIG. 4, so that alternate configurations resulting from a treatment sequence may be analyzed in terms of the pilot effluent for efficacy of the programmed treatment configuration. Thus, treated water emergent from the last step of a treatment configuration or sequence may be stored in tank 24 for use at pilot 60 and a second treatment sequence stored in tank 26 for use at pilot 62. As shown in FIG. 2, the pilot cooling towers may be replaced by pilot boilers.

THE LABORATORY

Referring to FIG. 4, the general area of the laboratory is designated by reference character 66. The analysis equipment may include a computer, an atomic adsorption spectrometer, chemical oxygen demand reactor, pH and conductivity analyzers and biological oxygen demand analyzers.

SUMMARY

The effluent from the on-site plant is to be subjected to treatment to determine if it can be so treated to be of a quality for reuse at the plant site which may be characterized by a water cooling tower or boiler. The laboratory supervisor will suggest a protocol or treatment sequence after analyzing the raw effluent. The protocol or treatment configuration may involve separation of contaminants, destruction of contaminants or both. There may be successive separations involving different species of treatment; equally so as destruction of contaminants; between successions, the sample, always an effluent but partly treated, is returned to a tank and pumped to the new treating unit featured in the treatment configuration. If it is determined by laboratory analysis the effluent can be revitalized as a useful source of water, the final sample is transmitted to a tank and from thence is pumped to the pilot simulator to be subjected to replication of the plant process. The water so employed as a replicate is finally analyzed to assure its efficacy, that is, water of a purity which can be indeed by reused at the plant.

We claim:

1. Apparatus for determining by audit whether effluent water released in an operating water treatment system, prevailing at a plant installation, and intended as an effluent for discharge to the environment, can be adequately treated to remove contaminants to an acceptable level so the effluent may be returned to the plant as reusable water, comprising an over-the road vehicle having a frame, a series of clean holding tanks removably supported by the frame of the vehicle, one of said holding tanks being a first clean holding tank assigned to receiving a sample of plant effluent water, a series of functionally different water treating units disposed on the frame of the vehicle above said holding tansk and into which the effluent sample can be pumped from said one of said holding tansk for treatment to reduce the contaminant level; pumps, manifolds, hosing and connectors supported by and beneath the frame of the vehicle and connected for:

pumping an effluent sample from one of said holding tanks directly to a selected treating unit for treatment; and
   returning the treated sample directly to a second clean holding tank for pumping from the second holding tank directly to either another treating unit for separate treatment or to a process simulator apparatus;
a laboratory within the vehicle for analyzing the treated effluent to determine if contaminants therein are reduced to a level where the effluent can be reused at the plant rather than discharged to the environment;
   process simulator apparatus selected from the group consisting of a pilot cooling tower and a pilot boiler within the vehicle allowing evaluation of the real time performance characteristics of the treated water; and
   said pumps, manifolds, connectors and hosing being so connected to feed treated water from one of said holding tanks to said process simulator apparatus where the corresponding plant process is run and evaluated on a real time basis using the treated water.

2. Apparatus according to claim 1 in which the treating units include at least one destructive treating unit for either eliminating organic contaminants, and in which the pumps, hoses, manifolds and connectors are so connected that the plant effluent is subjected to destructive treatment and thereafter delivered to a clean holding tank prior to transfer to said process simulator.

3. Apparatus according to claim 1 in which the treating units include at least one contaminant separation unit for removing solid contaminants and in which the pumps, hoses, manifolds and connectors are so connected that the plant effluent is subjected to separation treatment prior to transfer to said process simulator.

4. Apparatus according to claim 1 in which the treating units include at least one inhibition treating unit for subjecting the effluent to a scale inhibitor, and in which the pumps, hoses, manifolds and connectors and so connected that the plant effluent is subjected to scale inhibition and thereafter delivered to a clean holding tank prior to transfer to said process simulator.

5. Apparatus according to claim 1 in which the treating units include at least one clarifier treating unit to remove solid contaminants from the plant effluent and at least one destructive treating unit to remove organic contaminants from the plant effluent and at least one treating unit for applying a scale inhibitor to the plant effluent and in which the pumps, hoses, manifolds and connectors are so connected that of the three named treating units at least two are employed in succession with intermediate transfer of the treated effluent to a clean holding tank, and that following the last treatment the treated water is transferred to yet another clean holding tank and from thence to said process simulator.

6. A method of determining by real time audit if a raw water effluent released in a water treatment plant, having a water cooling tower or a boiler, can be effectively treated to remove contaminants so the effluent after such treatment can be reused at the plant comprising the following steps performed with apparatus supported an over-the-road vehicle for undertaking an audit of the effluent, and in which said vehicle includes a frame supporting a plurality of clean holding tanks supported removably beneath the frame of the vehicle and also a plurality of water treatment units housed by the vehicle above the frame;

(1) employing selectively connectable pumps, hoses, manifolds and connectors to connect the treating units and holding tansk in a predetermined succession representing a treatment protocol under the audit;
   (2) transferring a sample of the raw plant effluent to one of said holding tanks;
   (3) transferring the effluent sample from said one of said holding tansk to at least one of said water treatment units in accordance with the protocol and therein subjecting the transferred effluent sample to a treatment process to reduce the contaminant level;
   (4) analyzing the transferred effluent to determine if contaminants therein are reduced to a level where the effluent can be reused at the plant rather than discharged to the environment; and when the contaminant level has been reduced,
   (5) transferring the treated water to a process simulator in the vehicle, said process simulator selected from the group consisting of a pilot cooling tower and a pilot boiler, and using the transferred water to replicate the plant process son a real time basis using the treated water.

7. Method according to claim 1 in which the treating units include a separation treating unit for removing said contaminants from the plant effluent water and including the steps of:

(a) transferring the effluent to said separation treating unit for treatment, and following such treatment transferring the treated effluent to another one of said clean holding tanks prior to transferring the treated effluent to said process simulator.

8. Method according to claim 6 in which the treating units include a destructive treating unit to remove organic contaminants from the plant effluent water and including the steps of (a) transferring the effluent to said destructive treating unit for treatment, and following such treatment transferring the treated effluent to another one of said clean holding tansk prior to transferring the treated effluent to said process simulator.

9. Method according to claim 6 in which the treating units include a scale inhibition treating unit for treating the plant effluent water and further including the steps of:

(a) transferring the effluent from one of said holding tanks to said scale inhibitor treating unit for treatment, and following such treatment, transferring the treated effluent to another one of said clean holding tanks; and (b) transferring the treated effluent to said process simulator.

10. Method according to claim 6 in which the treating units include a separation treating unit to remove contaminants from the plant effluent water and a destructive treating unit to destroy organic material in the plant effluent water, and including the steps of:

(a) transferring the plant effluent from one of said holding tanks to one of the two named treating units and from thence to another clean holding tank;

(b) transferring the treated effluent to the second one of the two named treating units and from thence to another of said holding tanks; and (c) transferring the treated effluent from said another of said clean holding tansk to said process simulator.

* * * * *

UNITED STATES PATENT AND TRADEMARK OFFICE
CERTIFICATE OF CORRECTION

PATENT NO.  : 5,268,300
DATED       : December 7, 1993
INVENTOR(S) : William D. Lature, et al It is certified that error appears in the above-indentified patent and that said Letters Patent is hereby corrected as shown below:

```
Column 2, line 24, "a" should be --as--;

Column 5, line 14, "tansk" should be --tanks--;

line 16, "tansk" should be --tanks--;

Column 5, line 45, "either" should have been cancelled;

Column 6, line 23, "tansk" should be --tanks--;

line 27, "tansk" should be --tanks--;

line 46, "said" should be --solid--.
```

Signed and Sealed this

Third Day of May, 1994

Attest:

BRUCE LEHMAN

*Attesting Officer*    Commissioner of Patents and Trademarks